United States Patent [19]
Banta, Jr. et al.

[11] Patent Number: 5,798,461
[45] Date of Patent: Aug. 25, 1998

[54] METHODS AND APPARATUS FOR ULTRASOUND IMAGING USING COMBINED SCAN PATTERNS

[75] Inventors: Robert H. Banta, Jr., Andover, Mass.; Richard A. Snyder, Chester, N.H.; William J. Ossmann, Acton, Mass.

[73] Assignee: Hewlett-Packard Company, Palo Alto, Calif.

[21] Appl. No.: 655,521

[22] Filed: May 30, 1996

Related U.S. Application Data

[63] Continuation-in-part of Ser. No. 544,247, Oct. 17, 1995, which is a continuation of Ser. No. 71,423, Jun. 2, 1993, abandoned.

[51] Int. Cl.$^6$ .................................................. G01N 29/00
[52] U.S. Cl. ................................. 73/625; 73/628; 73/641
[58] Field of Search ............................... 73/625, 626, 628, 73/641

[56] References Cited

U.S. PATENT DOCUMENTS

| | | | |
|---|---|---|---|
| 4,070,905 | 1/1978 | Kossoff | 73/614 |
| 4,140,022 | 2/1979 | Maslak | 73/626 |
| 4,159,462 | 6/1979 | Rocha et al. | 340/1 R |
| 4,310,907 | 1/1982 | Tachita et al. | 367/11 |
| 4,319,489 | 3/1982 | Yamaguchi et al. | 73/626 |
| 4,344,327 | 8/1982 | Yoshikawa et al. | 73/626 |
| 4,368,643 | 1/1983 | Tachita et al. | 73/626 |
| 4,582,065 | 4/1986 | Adams | 73/626 |
| 4,664,122 | 5/1987 | Yano | 128/660 |
| 4,852,577 | 8/1989 | Smith et al. | 73/625 |
| 4,896,283 | 1/1990 | Hunt et al. | 364/577 |
| 4,937,797 | 2/1990 | Snyder et al. | 367/138 |
| 4,949,259 | 8/1990 | Hunt et al. | 364/413.25 |
| 4,962,667 | 10/1990 | Ogawa et al. | 73/626 |
| 5,123,415 | 6/1992 | Daigle | 128/661.01 |
| 5,148,810 | 9/1992 | Maslak et al. | 128/661.01 |
| 5,235,986 | 8/1993 | Maslak et al. | 128/661.01 |
| 5,261,408 | 11/1993 | Maslak et al. | 128/661.01 |
| 5,383,457 | 1/1995 | Cohen | 73/625 |

FOREIGN PATENT DOCUMENTS 3634504  4/1992  Germany.

*Primary Examiner*—George M. Dombroske
*Assistant Examiner*—Max H. Noori

[57] ABSTRACT

A composite scan pattern for ultrasound imaging includes a linear or curved linear scan pattern and one or more sector scan patterns. The sector scan patterns abut the linear or curved linear scan pattern along its boundaries to form the composite scan pattern. The linear or curved linear scan pattern can be steered to a desired angle $\theta$ for obtaining a high quality image. The sector apertures can be reduced in width and the linear scan pattern can be increased in width for imaging at shallow depths. The composite scan pattern provides a wide field of view for both shallow imaging and deep imaging.

32 Claims, 6 Drawing Sheets

METHODS AND APPARATUS FOR ULTRASOUND IMAGING USING COMBINED SCAN PATTERNS

CROSS REFERENCE TO RELATED APPLICATIONS

This application is a continuation-in-part of application Ser. No. 08/544,247 filed Oct. 17, 1995, which is a continuation of application Ser. No. 08/071,423 filed Jun. 2, 1993, now abandoned.

FIELD OF THE INVENTION

This invention relates to ultrasound imaging systems which utilize phased array beam steering and focusing and, more particularly, to methods and apparatus for ultrasound imaging which use a combination of linear or curved linear scanning and sector scanning to provide an increased field of view, while retaining the advantages of linear and curved linear scanning.

BACKGROUND OF THE INVENTION

In a phased array ultrasound imaging system, an ultrasound transducer includes an array of transducer elements. The system includes a multiple channel transmitter and a multiple channel receiver. In the typical case where the number of channels is less than the number of transducer elements in the array, an electronic switch network connects a selected group of transducer elements to the transmitter and receiver channels. Each transmitter channel causes a selected transducer array element to transmit an ultrasound pulse into an object being imaged, typically the human body. The transmitted ultrasound energy is steered and focused by applying appropriate delays to the pulses transmitted from each transducer array element so that the transmitted energy adds constructively at a desired point. The pulse is partially reflected back to the transducer array by various structures and tissues in the body.

Steering and focusing of the received ultrasound energy are effected in a reverse manner. The reflected ultrasound energy from an object or structure arrives at the array elements at different times. The received signals are amplified and delayed in separate receiver channels and then summed in a receive beamformer. The delay for each channel is selected such that the receive beam is focused at a desired point. The delays may be varied dynamically so as to focus the beam at progressively increasing depths along a scan line as the ultrasound energy is received. The transmitted beam is scanned over a region of the body, and the signals generated by the beamformer are processed to produce an image of the region.

Various scan patterns, or scan formats, are known in the prior art. In a linear scan pattern, ultrasound energy is transmitted and received along multiple parallel lines which originate at different points on the transducer array. The parallel lines may be perpendicular to the array or may be steered to a desired angle. The linear scan pattern produces a relatively high quality image, because all scan lines are incident upon structures being imaged from the same direction. The field of view obtained with a linear scan pattern is the same at all depths.

In a sector scan pattern, ultrasound energy is transmitted and received along sector lines which originate at a common apex, typically located on the transducer array. The sector scan pattern has a field of view that increases with depth. A disadvantage of the sector scan pattern is its relatively small field of view at shallow depths. Techniques for increasing the field of view of a sector scan pattern at shallow depths involving shifting the sector scan pattern to originate from a virtual apex located behind the transducer array are well known. The virtual apex scan patterns do not have the advantages of a linear scan in producing a high quality image.

A curved linear scan pattern is similar to a linear scan pattern in that the scan lines originate at different points along the transducer array. However, the face of the transducer array is curved rather than flat, or linear. The field of view of a curved linear scan pattern increases with depth at an angle that is limited by, though not necessarily equal to, the angle of arc subtended by the array.

A scanning technique which utilizes a combination of linear scan and sector scan is disclosed in U.S. Pat. No. 4,664,122 issued May 12, 1987 to Yano. In the disclosed transducer array, the scan format is realized by making the spacing between elements in subarrays at each end of the array less than the spacing between elements in a central subarray. Steering of the linear scan is not disclosed.

SUMMARY OF THE INVENTION

In accordance with the present invention, methods and apparatus for ultrasound imaging are provided. According to a first aspect of the invention, a method for ultrasound imaging in a system including an array of ultrasound transducer elements comprises the steps of transmitting ultrasound energy with the array along parallel lines originating at different points on the array and oriented, or steered, at an angle $\theta$ which may be variable with respect to a normal to the array, the parallel lines defining a linear scan pattern, and transmitting ultrasound energy with the array along sector lines originating from an apex, the sector lines defining a sector scan pattern. The sector scan pattern and the linear scan pattern abut to form a composite scan pattern. The method further includes receiving ultrasound echoes with the array along the parallel lines and the sector lines and providing signals representative of an image along the parallel lines and the sector lines.

The sector scan pattern can be utilized at one or both ends of the linear scan pattern. Typically, the apex of the sector scan pattern is located on the array at the end of the linear scan pattern. When sector scan patterns are utilized at both ends of the linear scan pattern, the composite scan pattern has a generally trapezoidal shape. The sector scan pattern extends between a desired maximum angle a with respect to a normal to the array and the angle $\alpha$ of the parallel lines.

The sector lines of the sector scan pattern are transmitted through a sector aperture of the array, and the parallel lines are transmitted through linear apertures of the array. In accordance with another aspect of the invention, the sector aperture in a composite scan pattern utilizing a linear scan pattern and a sector scan pattern is varied in width, depending on the depth of the region of interest. A full width sector aperture is used for relatively deep imaging, and a reduced width sector aperture that is narrower than the full width sector aperture is used for relatively shallow imaging. When the sector aperture is reduced in width for shallow imaging, the number of parallel lines in the linear scan pattern is preferably increased to provide a large field of view.

In a preferred embodiment, the transducer array comprises a linear array of equally-dimensioned and equally-spaced transducer elements. Preferably, the parallel lines are equally spaced and the sector lines are equiangularly spaced.

According to another aspect of the invention, there is provided a method for ultrasound imaging with a sector scan pattern in a system including an array of ultrasound transducer elements, a predetermined number of transmitter and receiver channels and an electronic switch for selecting transducer elements for connection to the transmitter and receiver channels. The method comprises the steps of determining, from a sector aperture size and a sector aperture location on the array, a mapping of the transducer elements to the transmitter and receiver channels, determining focusing delays from a sector angle and a focus for the sector scan pattern, converting the focusing delays to mapped focusing delays using the mapping, and transmitting and receiving ultrasound energy along sector scan lines of the sector scan pattern using the mapped focusing delays and providing signals representative of an image along the sector scan lines.

According to a further aspect of the invention, a method for ultrasound imaging is provided. Ultrasound energy is transmitted with an array of equally-spaced and equally-dimensioned ultrasound transducer elements along stepped scan lines originating at different points on the array. The stepped scan lines define a stepped scan pattern. Ultrasound energy is also transmitted with the array along sector scan lines originating from an apex of a sector scan pattern. Each of the sector scan lines of the sector scan pattern is transmitted through a sector aperture of the array. Each of the stepped scan lines of the stepped scan pattern is transmitted through a stepped aperture of the array. At an end of the stepped scan pattern, the sector aperture overlaps the stepped aperture, such that the sector scan pattern and the stepped scan pattern abut to form a composite scan pattern. Ultrasound echoes are received with the array along the stepped scan lines and the sector scan lines, and signals representative of an image along the stepped scan lines and the sector scan lines are provided. In one embodiment of the method, the array comprises a linear array, the stepped scan lines comprise parallel scan lines and the stepped scan pattern comprises a linear scan pattern. In another embodiment of the method, the array comprises a curved linear array, the stepped scan lines comprise curved linear scan lines and the stepped scan pattern comprises a curved linear scan pattern.

According to yet another aspect of the invention, an ultrasound imaging scanner is provided. The scanner comprises an array of equally-spaced and equally-dimensioned ultrasound transducer elements, a transmitter and a receiver. The transmitter transmits ultrasound energy with the array along stepped scan lines originating at different points on the array and along sector scan lines originating from an apex of a sector scan pattern. The stepped scan lines define a stepped scan pattern, and the sector scan lines define the sector scan pattern. The transmitter includes means for transmitting each of the sector scan lines of the sector scan pattern through a sector aperture of the array and means for transmitting each of the stepped scan lines of the stepped scan pattern through a stepped aperture of the array. At the end of the stepped scan pattern, the sector aperture overlaps the stepped aperture, such that the sector scan pattern and the stepped scan pattern abut to form a composite scan pattern. The receiver receives ultrasound echoes with the array along the stepped scan lines and the sector scan lines and provides signals representative of an image along the stepped scan lines and the sector scan lines. In one embodiment of the scanner, the array comprises a linear array and the transmitter includes means for transmitting ultrasound energy along parallel scan lines of a linear scan pattern. In another embodiment of the scanner, the array comprises a curved linear array and the transmitter includes means for transmitting ultrasound energy along curved linear scan lines of a curved linear scan pattern.

BRIEF DESCRIPTION OF THE DRAWINGS

For a better understanding of the present invention, reference is made to the accompanying drawings, which are incorporated herein by reference and in which.

DETAILED DESCRIPTION

Figure 1A:
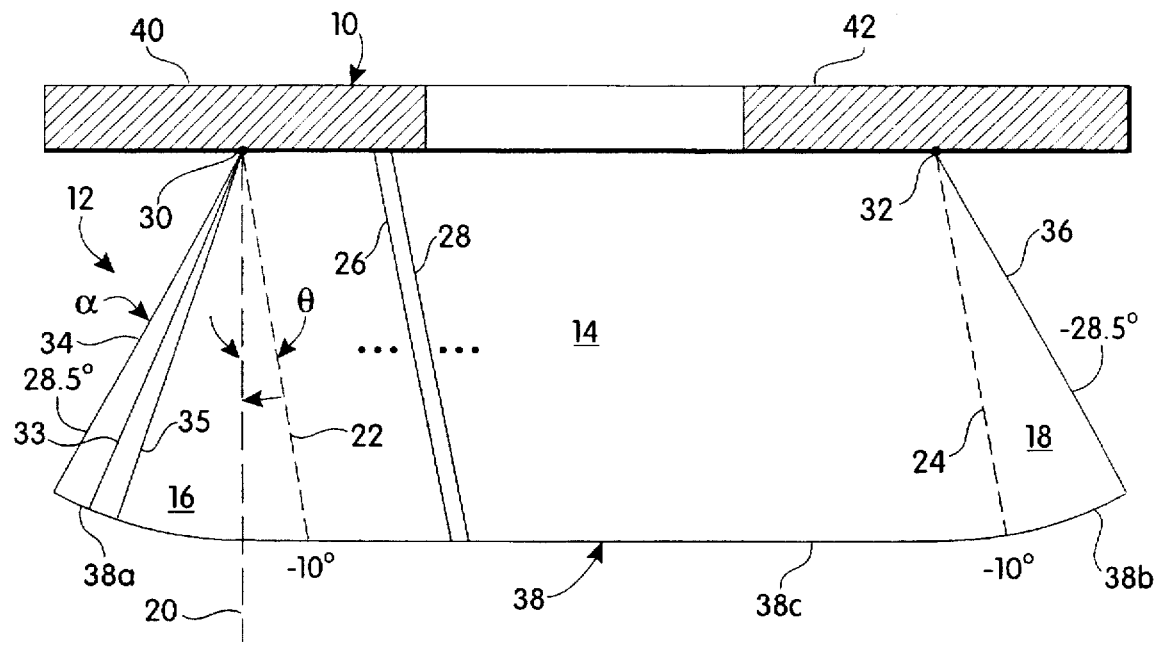
FIGS. 1A and 1B illustrate a scan pattern in accordance with the present invention for different linear scan angles.
Figure 1B:
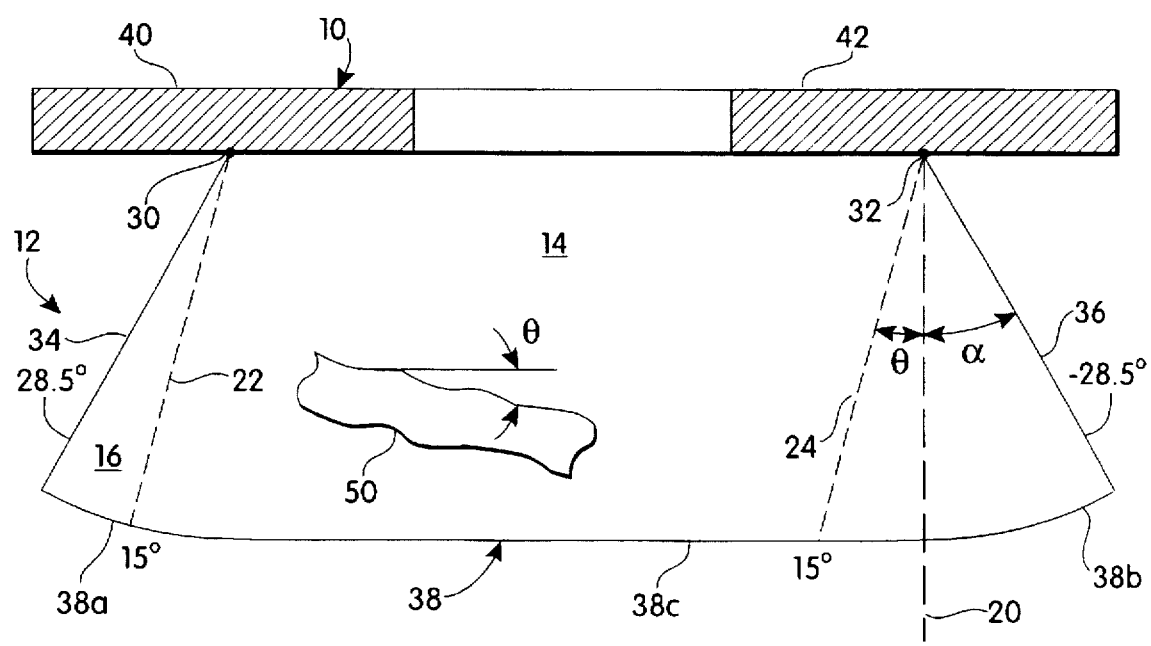

A technique for ultrasound imaging in accordance with one aspect of the present invention is illustrated in FIGS. 1A and 1B. An ultrasound transducer array 10 includes multiple transducer elements, typically in a linear configuration. Techniques for fabricating ultrasound transducer arrays are well known.

A composite scan pattern 12 includes a linear scan pattern 14 and sector scan patterns 16 and 18. The linear scan pattern 14 may be steered at an angle θ with respect to a normal 20 to array 10 and is bounded at its ends by lines 22 and 24. The linear scan pattern 14 is produced by multiple parallel scan lines 26, 28, etc. originating at different points on transducer 10. Each of the parallel lines may be oriented, or steered, at an angle θ with respect to normal 20 or may be parallel to normal 20. As used herein, "parallel scan lines" and "sector scan lines" refer to lines along which ultrasound energy is transmitted and received. The scan line can be defined as a line between the focal point and the center of the active transducer aperture, or, more particularly, the center of mass of the apodization function for the active transducer aperture.

Sector scan pattern 16 originates at apex 30 on transducer array 10, and sector scan pattern 18 originates at apex 32 on transducer array 10. The sector scan pattern 16 extends from a line 34, at an angle α with respect to normal 20, to line 22 at the boundary of linear scan pattern 14. Sector scan pattern 18 extends from a line 36, at an angle −α with respect to normal 20, to line 24 at the boundary of linear scan pattern 14. Sector scan pattern 16 is obtained by transmitting and receiving ultrasound energy along sector scan lines 33, 35, etc. originating at apex 30 and extending between lines 34 and 22. Typically, the sector lines are equiangularly spaced. Similarly, the sector scan pattern 18 is obtained by transmitting sector scan lines (not shown) originating at apex 32 and extending between lines 36 and 24. Thus, the sector scan pattern 16 abuts linear scan pattern 14 at one end, and the sector scan pattern 18 abuts linear scan pattern 14 at the other end.

The sector scan patterns 16 and 18 and the linear scan pattern 14 define composite scan pattern 12. The shape of composite scan pattern 12 is generally trapezoidal. The shape of scan pattern 12 is described as "generally trapezoidal" because the lower boundary 38 may not be a straight line. In FIGS. 1A and 1B, the lower boundary 38 includes curved portions 38a and 38b, and a straight portion 38c. Alternatively, the sector lines of sector scan patterns 16 and 18 can be extended such that the entire lower boundary of the composite scan pattern is a straight line.

Ultrasound energy is transmitted and received along the sector lines of sector scan patterns 16 and 18 and the parallel lines of linear scan pattern 14 through subarrays of the transducer elements in transducer array 10, known as apertures. The aperture through which ultrasound energy is being transmitted and received is known as the active aperture. In FIGS. 1A and 1B, sector scan patterns 16 and 18 are formed by transmitting and receiving ultrasound energy through sector apertures 40 and 42, respectively, indicated by the crosshatched portions of array 10. Each of the sector apertures 40 and 42 includes a sufficient number of transducer elements to produce the desired sector scan pattern. The apex of each sector scan pattern typically originates at the center of the respective sector aperture. In one example, described more fully below, the sector apertures 40 and 42 each include 128 transducer elements.

The linear scan pattern 14 extends from the apex 30 of sector scan pattern 16 at the center of sector aperture 40 to the apex 32 of sector scan pattern 18 at the center of sector aperture 42. Each of the parallel lines of linear scan pattern 14 has an associated linear aperture, as described below.

A typical scan of the composite scan pattern 12 can be performed as follows. Initially, ultrasound energy is transmitted and received by the transducer elements in sector aperture 40 along sector lines 33, 35, etc. originating at apex 30 to form sector scan pattern 16. The sector lines extend from line 34 at the maximum desired angle α to line 22 at the angle θ of linear scan pattern 14. In one example, the sector lines are spaced by ½ degree. Thus, in the example of FIG. 1A, the sector lines of sector scan pattern 16 extend from line 34 at 28.5° to a line at −9.50° adjacent to line 22 (since line 22 is the first line of the linear scan pattern 14). In this example, the sector scan pattern 16 has 76 sector lines. Alternatively, line 22 can be the last sector line of sector scan pattern 16, and the first line of the linear scan pattern 14 can be a line adjacent to line 22.

Next, the linear scan pattern 14 is formed by transmission and reception of ultrasound energy through linear apertures of array 10. The parallel lines of linear scan pattern 14 are formed by electronically shifting the active linear aperture across the array 10, typically by two transducer elements at a time. The first linear aperture used to form line 22 is typically the same as the sector aperture 40. Then, the linear aperture is shifted by two transducer elements, and ultrasound energy is transmitted and received along a second line parallel to line 22. The process of shifting the linear aperture by two transducer elements and transmitting and receiving ultrasound energy along parallel lines is repeated until completion of the linear scan pattern 14 at line 24. The linear scan pattern 14 thus comprises multiple scan lines parallel to lines 22 and 24 at the steering angle θ. It will be understood that the linear aperture can be shifted by one transducer element or by more than two transducer elements between parallel scan lines within the scope of the present invention.

Finally, the sector scan pattern 18 is formed in the same manner as sector scan pattern 16. That is, ultrasound energy is transmitted and received by the transducer elements of sector aperture 42 to form sector lines originating at apex 32. The sector lines extend between line 36 at the maximum desired angle and line 24 at the boundary of linear scan pattern 14. It will be understood that the sequence for scanning the sector scan patterns and the linear scan pattern is arbitrary and that a different sequence can be used. Preferably, however, scanning is sequential from left to right or from right to left.

The received ultrasound echoes along each of the sector lines and the parallel lines are converted to electrical signals by the transducer elements of the active aperture. The electrical signals are processed as described below to provide an ultrasound image of the region within composite scan pattern 12. The image is typically presented on a display screen and has the shape of the scan pattern 12 shown in FIGS. 1A and 1B and described above.

The scan pattern 12 shown in FIGS. 1A and 1B and described above, which includes both a steered linear scan pattern and one or more sector scan patterns, has a number of advantages over prior art scan patterns. The steered linear scan pattern 14 provides a high quality image of structures of interest, because the angle θ of scan pattern 14 can be adjusted for perpendicular incidence on a structure of interest. For example, as shown in FIG. 1B, when a blood vessel 50 under study is oriented at an angle θ with respect to transducer array 10, the linear scan pattern 14 can be steered to angle θ for the best image. The sector scan patterns 16 and 18 greatly increase the field of view.

An example of transducer array 10 includes 288 elements with an element pitch (center to center spacing) of 135 micrometers, which corresponds to 0.66 of the ultrasound wavelength at 7.5 MHz and 0.44 of the ultrasound wavelength at 5.0 MHz. This configuration permits steering of ultrasound energy to at least ±30 degrees and allows a smooth transition between the sector scan pattern and the linear scan pattern. For a transducer array 10 having 288 elements and a long dimension of 3.89 cm, the scan width for a conventional linear scan is 3.4 cm at all depths. When the linear scan is combined with sector scan in accordance with the present invention, the field of view increases with depth. In the above example for sector angles of 28.5° and using variable sector apertures as discussed below, the field of view at a 4 cm depth is 6.8 cm; the field of view at a 6 cm depth is 8.3 cm; and the field of view at an 8 cm depth is 9.8 cm.

It will be understood that numerous variations are included within the scope of the present invention. For example, it is not necessary to provide sector scan patterns at both ends of the linear scan pattern. Instead, a single sector scan pattern may be provided at either end of the linear scan pattern. When sector scan patterns are utilized at both ends of the linear scan pattern, they may have different parameters. For example, the sector scan patterns may have different maximum angles and may be transmitted through different sector apertures. Furthermore, the apex of the sector scan pattern is not necessarily located on the transducer array 10. Techniques for generating a sector scan pattern which originates from a virtual apex located behind or in front of the transducer array 10 may be employed within the scope of the present invention. The parameters of the transducer array, including the number of transducer elements and the element pitch, can be selected for a particular application.

As a further variation, transmit splice techniques can be utilized. According to transmit splice techniques, two scan lines are transmitted sequentially in the same direction and from the same origin on the array, but at different focal depths. This process is repeated for each scan line in the desired scan pattern.

According to another aspect of the invention, the sector apertures 40 and 42 are varied in width, depending on the depth of the region of interest. Typically, the image depth is selected based on the depth of the region of interest. As noted above, sector scan patterns have a relatively small field of view at shallow depths and a relatively large field of view at greater depths. The linear scan pattern has a fixed field of view at all depths. These features are used to provide a large of view for both shallow and deep imaging. A large aperture allows detailed resolution of deep structures. At shallow imaging depths, the sector apertures may be reduced in width, and the width of the linear scan pattern may be increased by increasing the number of parallel lines. By increasing the width of the linear scan pattern, the field of view is increased at shallow imaging depths.

Figure 2A:
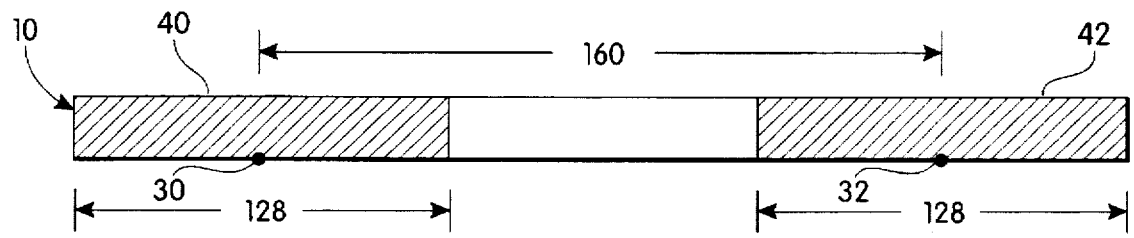
FIGS. 2A–2C are schematic representations of the transducer array and illustrate variation of the scan pattern for different imaging depths.
Figure 2B:
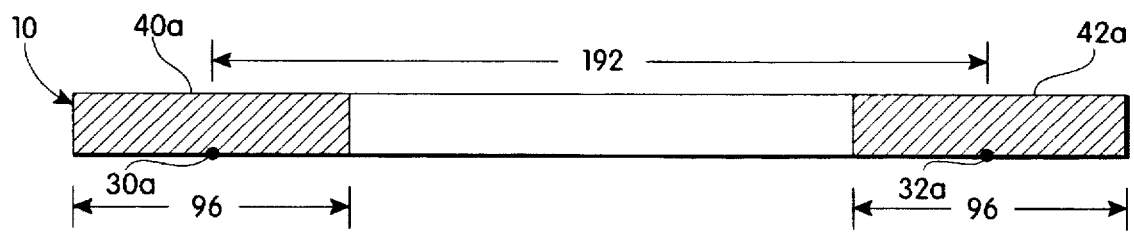
Figure 2C:
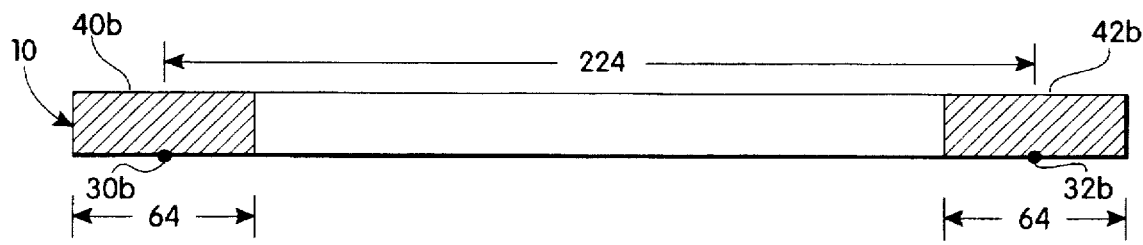

Variation of the width of each sector aperture and the width of the linear scan pattern is illustrated in FIGS. 2A–2C. In FIG. 2A, the sector apertures 40 and 42 of transducer array 10 are at full width, and the linear scan pattern extends between apex 30 and apex 32. In one example of the present invention, the transducer array 10 has 288 elements and the sector apertures 40 and 42 each have 128 transducer elements. The linear aperture also has 128 elements and is typically displaced two elements at a time from apex 30 to apex 32 to form 81 parallel lines. The configuration shown in FIG. 2A is suitable for imaging depths of about 8 cm or greater.

The configuration shown in FIG. 2B is suitable for intermediate imaging depths, such as about 6 cm. The sector apertures 40a and 42a are reduced in width in comparison with sector apertures 40 and 42 shown in FIG. 2A. Ultrasound energy is transmitted and received along sector lines originating at apexes 30a and 32a, which are displaced outwardly toward of the ends of transducer array 10 in comparison with apexes 30 and 32 shown in FIG. 2A. The linear scan pattern extends between apex 30a and apex 32a. In the above example of a transducer array 10 having 288 elements, the sector apertures 40a and 42a each have 96 elements, and the linear scan pattern includes 97 parallel lines.

A configuration for shallow imaging at depths of about 4 cm is illustrated in FIG. 2C. Sector apertures 40b and 42b are reduced to minimum width, and the linear scan pattern is increased to maximum width. The sector scan patterns originate from apexes 30b and 32b, which are displaced closer to the ends of transducer array 10. In the example of a transducer array having 288 elements, the sector apertures 40b and 42b each have 64 elements, and the linear scan pattern has 113 parallel lines.

In the example of FIG. 2A, the sector apertures 40 and 42 have 128 transducer elements each, and the linear apertures for transmitting the parallel lines of the linear scan pattern have 128 transducer elements for each of the parallel lines. When the sector apertures are reduced in width, as shown in FIGS. 2B and 2C, the width of the linear aperture is preferably reduced near of the ends of the linear scan pattern. With reference to FIG. 2B, the linear aperture is reduced to the width of the sector aperture for transmission and reception of ultrasound energy along a line originating at apex 30a. The linear aperture is then displaced along the array by two elements at a time and is increased in width by four elements for each successive scan line until it reaches the desired maximum width in the central portion of array 10. The linear aperture is then reduced in width by four elements for each successive scan line as it approaches apex 32a and has the width of sector aperture 42a for transmission and reception of ultrasound energy along a line originating at apex 32a. As the active linear aperture approaches the end of the linear scan pattern, two transducer elements are preferably removed from both the leading edge and the trailing edge of the aperture for each successive scan line to reduce the aperture symmetrically. Similarly, as the active linear aperture moves away from the end of the linear scan pattern, two transducer elements are added to both the leading edge and the trailing edge of the aperture for each successive scan line until the aperture reaches its maximum width. This keeps the transmit beam parallel to the receive beam.

Alternatively, asymmetric linear apertures can be used near the ends of the linear scan pattern, with some degradation of image quality away from the transmit focus. In this case, as the active linear aperture reaches the end of the array, the leading channels simply fall off the end and are not used. Furthermore, asymmetric sector apertures may be used in order to locate the apex of the sector scan pattern at or near the end of the transducer array. In each case, the sector scan pattern and the linear scan pattern abut to define a contiguous composite scan pattern.

In the example of FIG. 2B where the sector apertures 40a and 42a have 96 elements each, the linear aperture varies from 96 elements at the ends of the linear scan pattern to 128 elements in the central portion of linear scan pattern. Similarly, with respect to the example of FIG. 2C, the linear aperture varies from 64 elements at the ends of the linear scan pattern to 128 elements in the central portion of the linear scan pattern.

It will be understood that the number of elements in the array, the number of elements in the sector apertures, the number of elements in the reduced width sector apertures and the number of elements in the linear apertures shown in FIGS. 2A and 2C and described above are given by way of example only, and that other array and aperture sizes are included within the scope of the present invention. Furthermore, the relative sizes of the linear aperture and the sector apertures are a matter of design choice. Depending on the relative widths of the sector aperture and the linear aperture, it may not be necessary to reduce the width of the linear aperture near the ends of the linear scan pattern as described above.

Figure 3:
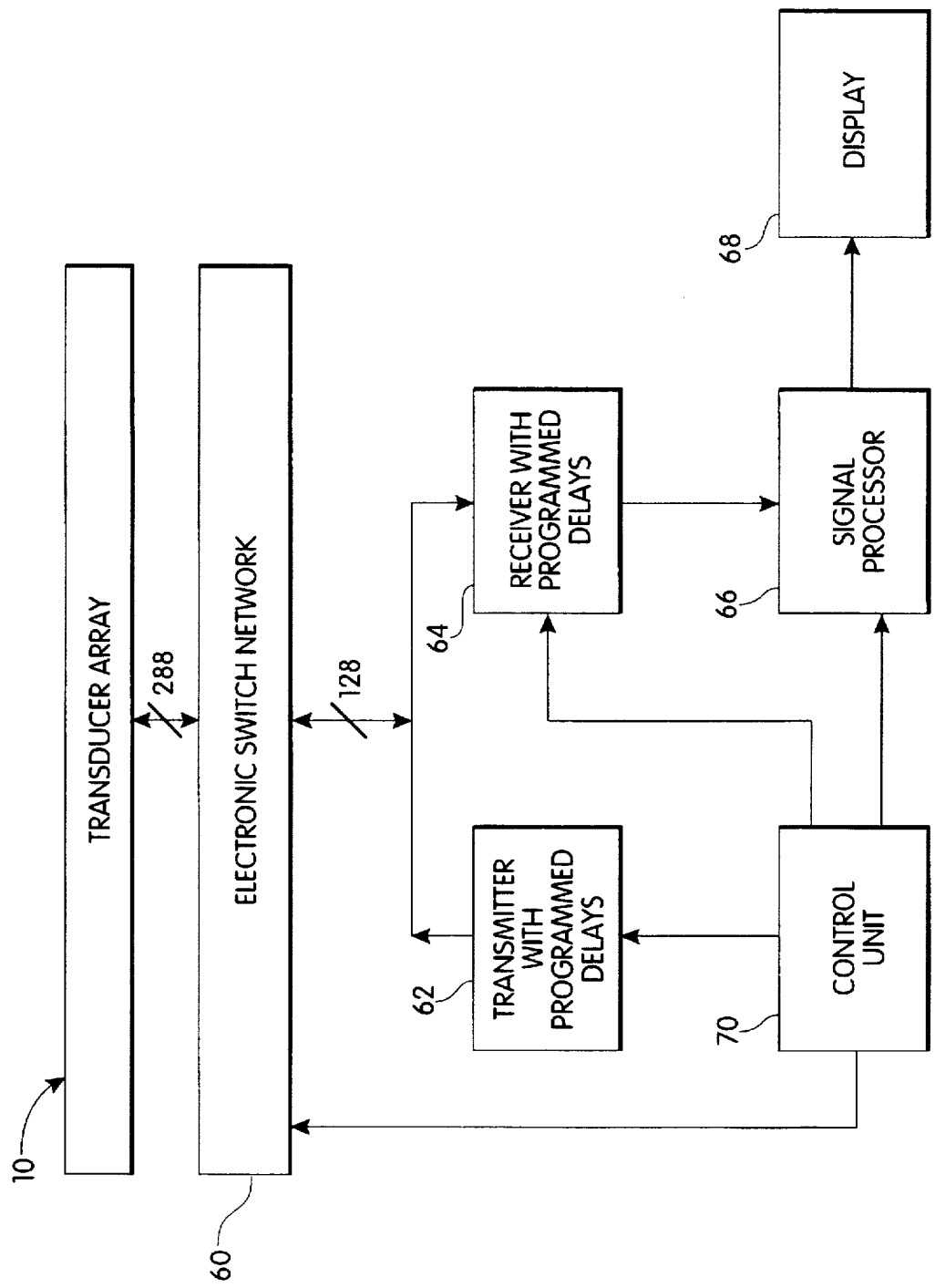
FIG. 3 is a simplified block diagram of an ultrasound imaging system for implementing the present invention.

A simplified block diagram of an example of an ultrasound imaging system suitable for implementing the scanning techniques described above is shown in FIG. 3. The transducer elements of array 10 are each connected to an electronic switch network 60 which defines an active sector aperture or linear aperture by selecting a group of transducer elements for transmitting and receiving ultrasound energy. In the example of FIG. 3, the transducer array 10 has 288 elements, and the maximum aperture size is 128 elements. Electronic switch network 60 couples the selected transducer elements to a transmitter 62 having one transmitter channel for each transducer element in the selected aperture. The transmitter channels have programmable delays for steering and focusing the transmitted ultrasound energy. The transmitter 62 provides appropriately delayed ultrasonic pulses through the electronic switch network 60 to the selected transducer elements of the sector aperture or the linear aperture.

The selected transducer elements of the aperture are also connected by electronic switch network 60 to a receiver 64 having one receiver channel for each transducer element in the selected aperture. The receiver 64 delays the received signals from each transducer element of the selected aperture to effect focusing and steering, and combines the delayed signals to produce signals representative of an image along the sector lines and the parallel lines of the composite scan pattern 12 (FIGS. 1A and 1B). The signals are supplied through a signal processor 66 to a display 68, typically a CRT, for display of the ultrasound image. Preferred scan conversion techniques used by the signal processor 66 are disclosed in U.S. Pat. No. 4,896,283, issued Jan. 23, 1990 to Hunt et al., which is hereby incorporated by reference. The display 68 provides a display, as shown schematically in FIGS. 1A and 1B, of the image space. A control unit 70 supplies control signals to the switch network 60 for selection of transducer elements, to the transmitter 62 and the receiver 64 for selection of delays and to the signal processor 66 for control of the image display.

The switch network 60 can be considered a multiplexer between the transducer elements and the processing electronics. A preferred multiplexer is a "tractor treading" multiplexer, as known to those skilled in the art. For a phased array system, each of the received transducer signals must be processed in a precise manner, typically using predetermined phase compensations and delay tap selections in the processing electronics. These phase and tap variables are related to the elements' relative position in the selected apertures. A preferred technique for implementing delays utilizing heterodyning means (mixers) and tapped delay lines is disclosed in U.S. Pat. No. 4,140,022, issued Feb. 20, 1979 to Maslak, which is hereby incorporated by reference. A delay coefficient generator for determining delay coefficients to be used during dynamic focusing is disclosed in U.S. Pat. No. 4,949,259 issued Aug. 14, 1990 to Hunt et al, which is hereby incorporated by reference. Known techniques for transmit apodization and dynamic receive apodization can be used in the system of FIG. 3. A system suitable for implementation of the scan patterns of the present invention is the Sonos 1000 system manufactured and sold by Hewlett-Packard Company.

It will be understood that the present invention is not limited to implementation in an ultrasound imaging system of the type shown in FIG. 3 and described above. For example, where the number of channels in the transmitter and the receiver is equal to the number of transducer elements in the array, the electronic switch network 60 is not required. In this case, selected transmitter and receiver channels are activated to produce a desired aperture. Also, the scanning technique of the present invention can be implemented in a digital receive beamformer wherein the received signals are digitized and then delayed digitally.

Figure 4:
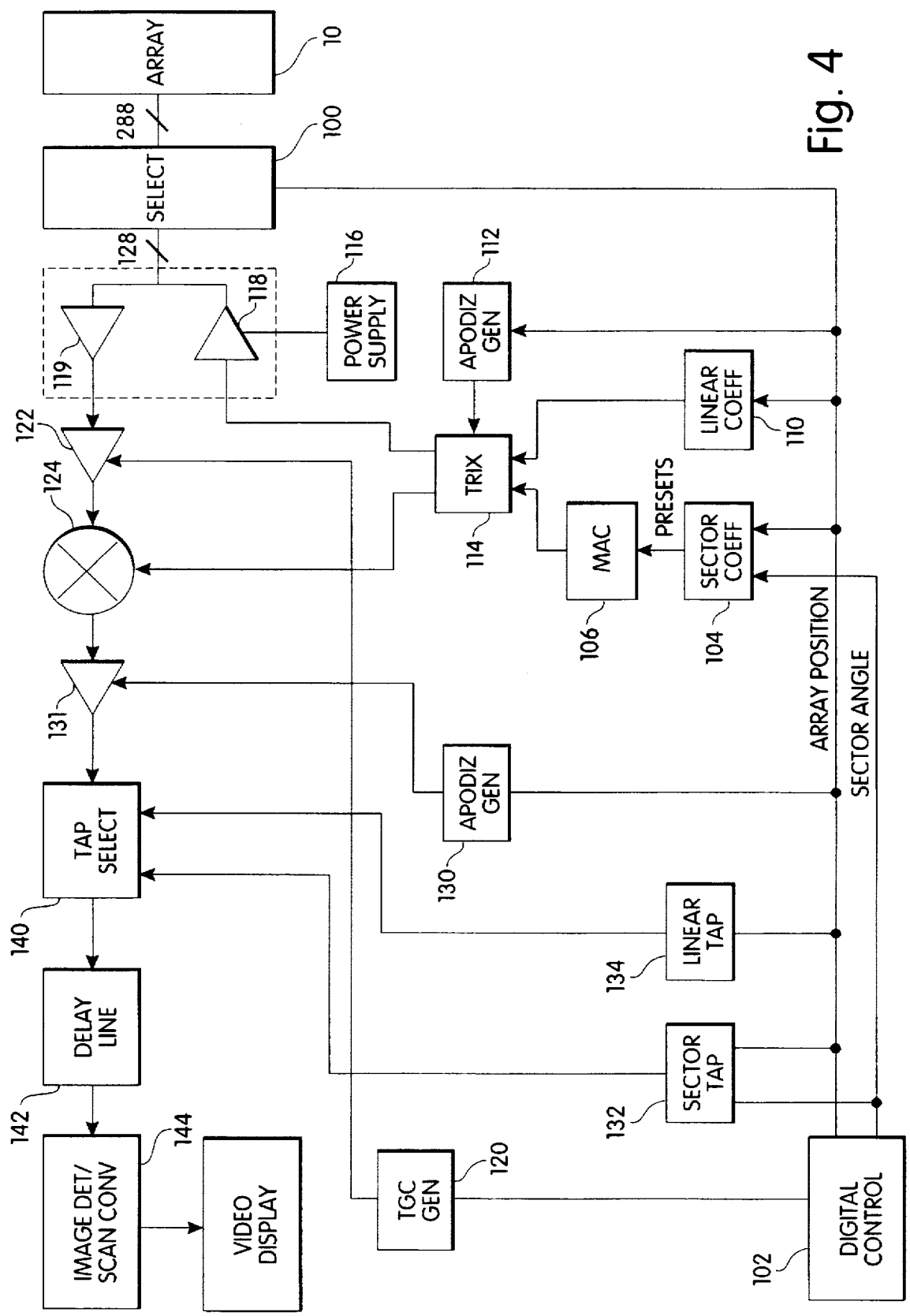
FIG. 4 is a block diagram of a preferred embodiment of an ultrasound imaging system for implementing the present invention.

A block diagram of a preferred embodiment of an ultrasound imaging system for implementing the present invention is shown in FIG. 4. The basic architecture is based on the aforementioned U.S. Pat. No. 4,140,022 and employs a so-called mix and delay (fine delay added to coarse delay) mechanism for focusing and steering. A select circuit 100 (which corresponds to the electronic switch network 60 shown in FIG. 3 and described above) connects the system transmitter and receiver channels to the transducer elements of the array 10. In the example described above, the system includes 128 channels, and the array 10 includes 288 transducer elements. The select circuit 100 performs tractor treading. The system shown in FIG. 4 also includes both sector and linear focusing circuits to generate sector scan patterns and linear scan patterns as described above.

A digital control 102 determines, for each scan line, the operating mode (sector or linear) and the location of the active aperture on the array 10. For sector mode, the digital control 102 also determines the angle a of the sector line. A sector coefficient generator 104 on transmit, when enabled in the sector mode, generates coefficients of a third order polynomial, which is a series approximation of the distance formula from a transducer element for the chosen focal point and sector angle, as disclosed in the aforementioned U.S. Pat. No. 4,949,259. The coefficients are then rotated into alignment with the active aperture, as determined by the select circuit 100, and passed to a MAC circuit 106 as presets. The MAC circuit 106 generates the delay values for each channel, as disclosed in U.S. Pat. No. 4,949,259. A linear coefficient generator 110 on transmit, when enabled in linear mode, generates the delays for each channel for the chosen focal point and linear angle. The delays are then rotated into alignment with the active aperture, as determined by the select circuit 100. A transmit apodization generator 112 generates the transmit apodization profile for the chosen transmit focal point. The profile is then rotated into alignment with the active aperture, as determined by the select circuit 100. A transmit control circuit (TRIX) 114 loads the delay for each channel into a countdown counter. After the counter reaches a terminal count, the TRIX 114 generates a transmit pulse if it is enabled by the transmit apodization generator 112. A power supply 116 supplies high voltage to transmit drivers 118.

The received signal is supplied by select circuit 100 to a preamplifier 119. A TGC generator 120 provides time gain control to a variable gain amplifier 122 in each receive channel, as known in the art. The sector coefficient generator 104 on receive, when enabled in sector mode, is used to generate receive coefficient presets for each focal zone. The coefficient presets are used by the MAC circuit 106 to generate receive delays. The linear coefficient generator 110 on receive, when enabled in linear mode, is used to generate receive delays for each focal zone. The TRIX 114 on receive generates mixer control signals for a mixer 124 in each receive channel. A receive apodization generator 130 applies a dynamic receive apodization profile to a variable gain amplifier 131. The profile is rotated into alignment with the active aperture, as determined by the select circuit 100, before being applied to the receive channels. A sector tap generator 132, when enabled in the sector mode, generates tap control signals for the chosen focal point and sector angle. The tap control signals are rotated into alignment with the active aperture, as determined by the select circuit 100. A linear tap generator 134, when enabled in the linear mode, generates tap control signals for the chosen focal point and linear angle. The tap control signals are then rotated into alignment with the active aperture, as determined by the select circuit 100. A tap selector 140 selects a tap on a summing delay line 142. Alternatively, the tap selector 140 can configure the delay line, depending on the particular implementation used, to provide an appropriate delay for the scan line. An image detector/scan converter 144 scan converts the detected signal using scan conversion techniques disclosed in the aforementioned U.S. Pat. No. 4,896,283 to display an ultrasound image on a video display screen.

Figure 5:
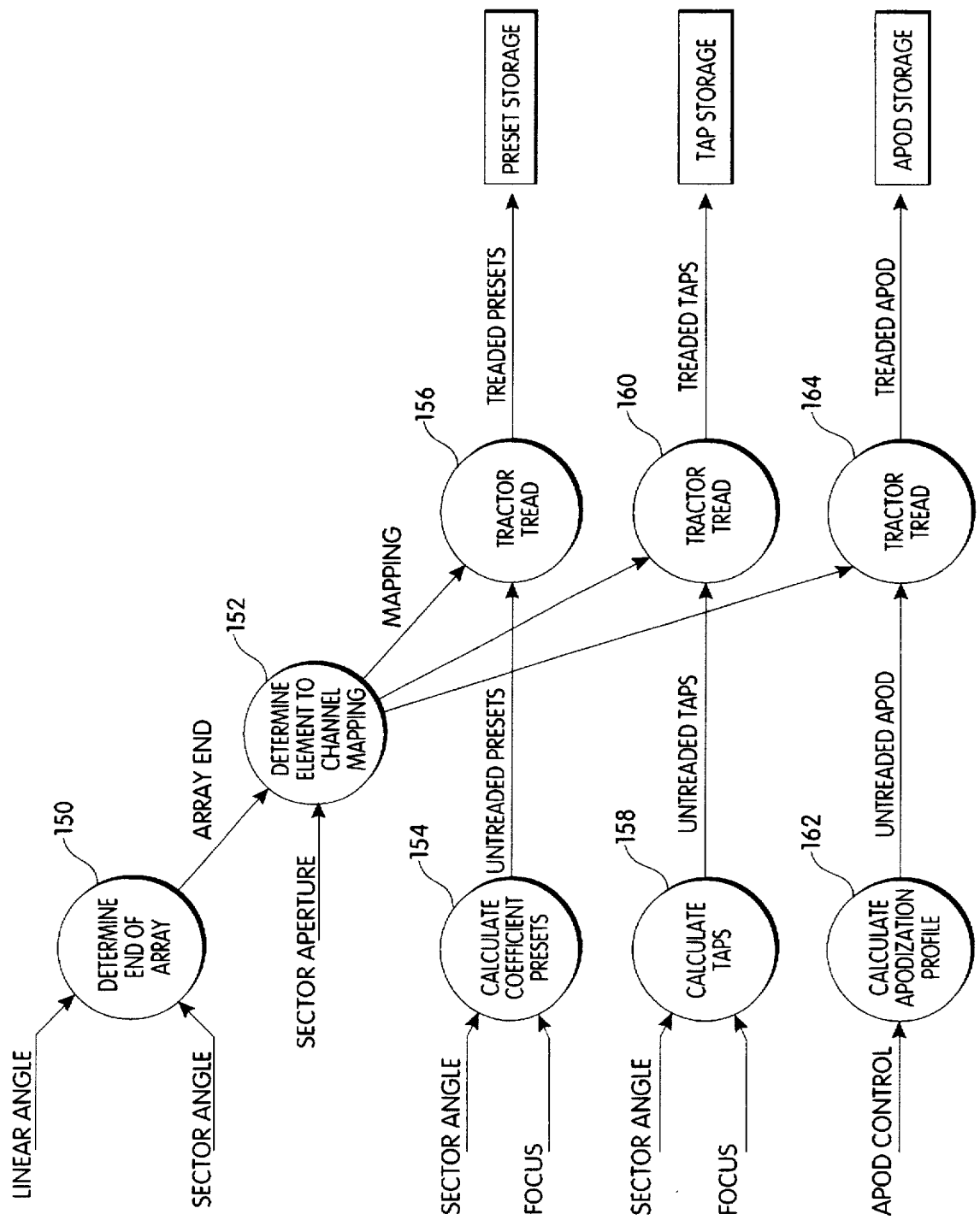
FIG. 5 is a flow diagram which illustrates the steps associated with generating a sector scan pattern at one or both ends of a linear scan pattern in the system of FIG. 4.

The steps involved in transmitting and receiving ultrasound energy along the sector lines of a sector scan pattern originating from a sector aperture near one end of the transducer array 10 are shown in FIG. 5. With reference to FIG. 4, the steps are performed by the digital control 102, which can be a microprocessor, and the results are loaded into the sector coefficient generator 104, the apodization generators 112 and 130 and the sector tap generator 132, which can include random access memories. In step 150, the location of the sector aperture, i.e., which end of the array 10, is determined from the sector angle and the linear angle. When the angle of the sector line is greater than the angle of the linear line, then the sector aperture is on the left side of the array 10. Otherwise, the sector aperture is on the right side of the array. In step 152, a mapping of transducer elements to transmitter and receiver channels is determined from the size of the sector aperture and the location of the sector aperture. The mapping is required because the tractor treading process produces a rotation in the correspondence between transducer elements and system channels. In step 154, coefficient presets are generated in accordance with U.S. Pat. No. 4,949,259 for transmit and receive focal points and for the required sector angle. In step 156, the coefficient presets are mapped in accordance with the previously determined mapping to provide mapped coefficient presets, which are stored in sector coefficient generator 104 (FIG. 4). In step 158, tap control signals are determined for the indicated focal point and the required sector angle. The tap control signals are mapped in step 160 to provide mapped tap control signals, which are stored in sector tap generator 132. In step 162, transmit and receive apodization profiles are generated based on apodization control signals. The unmapped apodization profiles are mapped in step 164 and stored in the transmit apodization generator 112 and the receive apodization generator 130, respectively.

It will be understood that the embodiment of the ultrasound imaging system shown in FIGS. 4 and 5 and described above is one example of a suitable system for implementation of the present invention and that other implementations can be utilized as described above.

Figure 6:
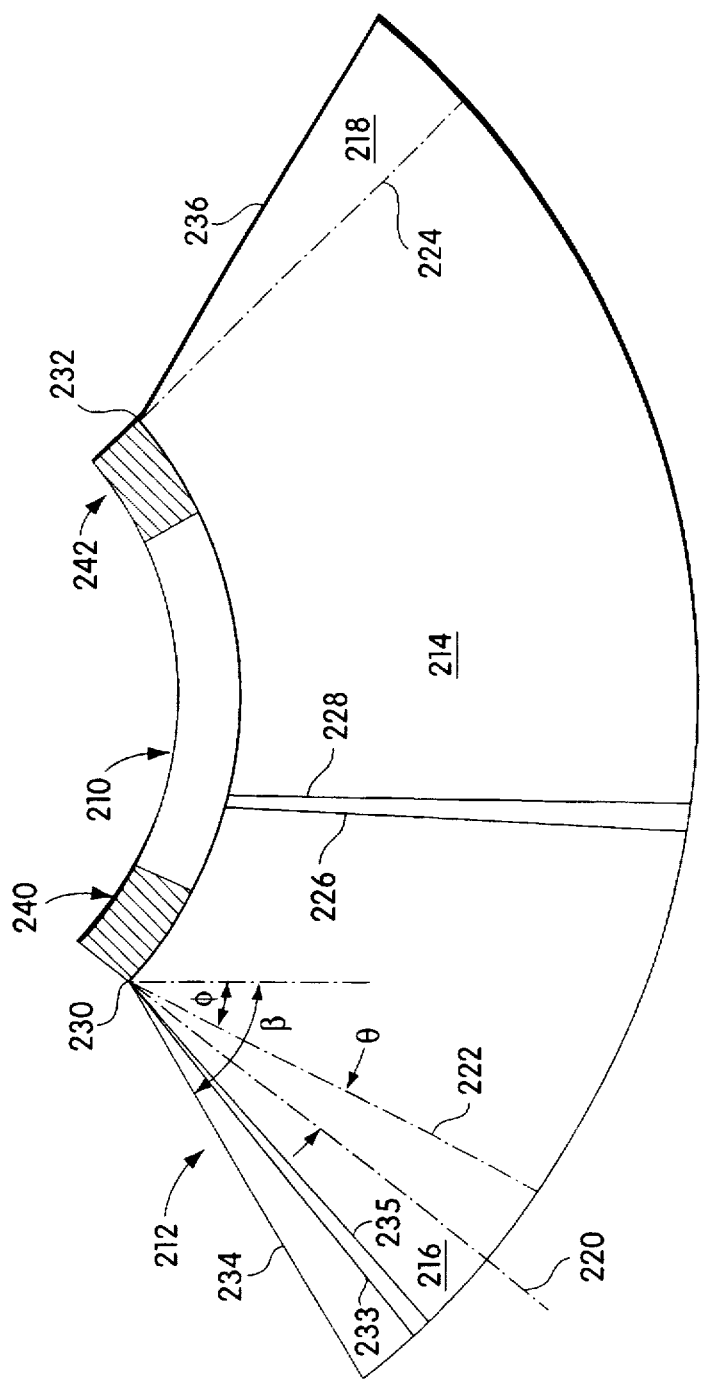
FIG. 6 illustrates a curved linear scan pattern in accordance with the present invention.

The method described above with reference to FIGS. 1A and 1B may be applied to curved linear scan patterns as shown in FIG. 6. As used herein, "curved linear" scanning refers to ultrasound scanning with a curved array of transducer elements, as shown in FIG. 6, wherein an active aperture is incrementally shifted, or stepped, across the curved array, and ultrasound energy is transmitted and received with each active aperture. Curved linear scan patterns and linear scan patterns may be referred to generally as "stepped" scan patterns, because both involve stepping an active aperture across the array.

The linear scan pattern 14 is replaced with a curved linear scan pattern 214, whose scan lines are not parallel, but form a constant angle θ with respect to the normal to the curved array 210. Sector scan patterns 216 and 218 are located at the ends of the curved linear scan pattern 214. Asymmetric apertures 240, 242 are typically used at the ends of the curved linear scan pattern 214 and for the sector scan patterns 216, 218, allowing the sector scan lines to originate from apices 230, 232 that are located at or near the extreme ends of the array 210.

A typical scan of the curved linear composite scan pattern 212 can be performed as follows. Initially, ultrasound energy is transmitted and received by the transducer elements in sector aperture 240 along sector lines 233, 235, etc. originating at apex 230 to form sector scan pattern 216. The sector lines extend from line 234 at the maximum desired angle β to line 222 at the angle φ of the curved linear scan pattern 214, which may be steered at an angle θ with respect to the normal 220 to the array 210. In one example, the sector lines are spaced by 0.4 degree. Thus, in the example of FIG. 6, the sector lines of sector scan pattern 216 extend from line 234 at 50° to a line at 30.4° adjacent to line 222 (since line 222 is the first line of the curved linear scan pattern 214). In this example, the sector scan pattern 216 has 50 sector lines.

Next, the curved linear scan pattern 214 is formed by transmission and reception of ultrasound energy through curved linear apertures of array 210. The lines of the curved linear scan pattern 214 are formed by electrically shifting the active curved linear aperture across the array 210, typically by one transducer element at a time. The first curved linear aperture used to form line 222 is typically the same as the sector aperture 240. Then the curved linear aperture is shifted by one transducer element, and ultrasound energy is transmitted and received along a second line adjacent to line 222. The process of shifting the curved linear aperture by one element and transmitting and receiving ultrasound energy along sequential lines is repeated until completion of the curved linear scan pattern 214 at line 224. The curved linear scan pattern 214 thus comprises multiple scan lines at the steering angle θ. It will be understood that the curved linear aperture can be shifted by a fraction of one element or by more than one element within the scope of this invention.

Finally, the sector scan pattern 218 is formed in the same manner as sector scan pattern 216. That is, ultrasound energy is transmitted and received by the transducer elements of sector aperture 242 to form sector lines originating at apex 232. The sector lines extend between line 236 at the maximum desired angle and line 224 at the boundary of curved linear scan pattern 214. It will be understood that the sequence for scanning the sector scan patterns and the curved linear scan pattern is arbitrary and that a different sequence can be used. Preferably, however, scanning is sequential from left to right or from right to left.

The received ultrasound echoes along each of the sector lines and the lines in the curved linear scan pattern are converted to electrical signals by the transducer elements of the active aperture. The electrical signals are processed as described previously with reference to the composite linear scan pattern to provide an ultrasound image of the region within composite scan pattern 212. The image typically is presented on a display screen and has the shape of the scan pattern 212 shown in FIG. 6 and described above.

The scan pattern 212 shown in FIG. 6 and described above, which includes both a curved linear scan pattern and one or more sector scan patterns, has the advantage over prior art scan patterns of a wider field of view. As an example, the transducer array 210 may have a radius of curvature of 40 millimeters and include 192 elements with an element pitch (center to center spacing) of 275 micrometers, which corresponds to 0.625 of the ultrasound wavelength at 3.5 MHz. This configuration permits steering of the ultrasound energy to at least ±30 degrees and allows a smooth transition between the sector scan pattern and the curved linear scan pattern. For a transducer array 210 having 192 elements on a pitch of 275 micrometers and a 40 millimeter radius of curvature, the angular size of a conventional scan is 75 degrees. When the curved linear scan is combined with sector scan in accordance with the present invention, the field of view is increased. In the above example, for sector angles of 20 degrees, the angular size of the scan is increased to 115 degrees. Then at a depth of 50 mm from the face of the array, the composite scan pattern has a width of 232 mm compared to 138 mm for the conventional scan pattern.

It will be understood that numerous variations are included within the scope of the present invention. For example, it is not necessary to provide sector scan patterns at both ends of the curved linear scan pattern. Instead, a single sector scan pattern may be provided at either end of the curved linear scan pattern. When sector scan patterns are utilized at both ends of the curved linear scan pattern, they may have different parameters. For example, the sector scan patterns may have different maximum angles. Furthermore, the apex of the sector scan pattern is not necessarily located on the transducer array 210. Techniques for generating a sector scan pattern which originates from a virtual apex located behind or in front of the transducer array 210 may be employed within the scope of the present invention. The parameters of the transducer array, including the number of transducer elements and the element pitch, can be selected for a particular application.

The above description of curved linear scanning and sector scanning in accordance with the present invention is directed to the general case where the curved linear scan lines are steered at an angle θ with respect to the normals to the array 210. In many practical applications, the angle θ is zero and the curved linear scan lines coincide with normals to the curved linear array. It will be understood that the direction of the normal to the curved linear array varies with position on the array. Thus, the directions of the curved linear scan lines vary as the curved linear aperture is shifted across the array.

The composite scan pattern shown in FIG. 6 and described above can be generated with the ultrasound imaging system shown in FIGS. 3–5 and described above, with appropriate changes in the transmit delays to transmit ultrasound energy along the required sector scan lines and curved linear scan lines and changes in the receive delays to focus received energy along the along the required sector scan lines and curved linear scan lines.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for ultrasound imaging, comprising the steps of:
   transmitting ultrasound energy with an array of equally-spaced and equally-dimensioned ultrasound transducer elements along parallel lines originating at different points on said array and oriented at a nonzero angle θ with respect to a normal to the array, said parallel lines defining a linear scan pattern;
   transmitting ultrasound energy with said array along sector lines originating from an apex, said sector lines defining a sector scan pattern, wherein each of the sector lines of said sector scan pattern is transmitted through a sector aperture of said array, wherein each of the parallel lines of said linear scan pattern is transmitted through a linear aperture of said array and wherein, at an end of the linear scan pattern, the sector aperture overlaps the linear aperture such that said sector scan pattern and said linear scan pattern abut to form a composite scan pattern in which said sector scan pattern and said linear scan pattern are nonoverlapping; and
   receiving ultrasound echoes with said array along said parallel lines and said sector lines and providing signals representative of an image along said parallel lines and said sector lines.

2. A method as defined in claim 1 wherein the apex of said sector scan pattern is located on said array and coincides with the end of said linear scan pattern.

3. A method as defined in claim 2 wherein the step of transmitting along sector lines includes transmitting along sector lines between a desired maximum angle α with respect to a normal to the array and the angle θ of the parallel lines.

4. A method as defined in claim 1 wherein the step of transmitting along sector lines includes transmitting along sector lines to form sector scan patterns at both ends of the linear scan pattern so that said composite scan pattern has a generally trapezoidal shape.

5. A method as defined in claim 1 further including the step of varying the width of said sector aperture and the width of said linear scan pattern, depending on the depth of a region of interest.

6. A method as defined in claim 5 wherein the step of varying the width of said sector aperture and the width of said linear scan pattern includes providing a wide sector aperture and a narrow linear scan pattern for relatively deep imaging and providing a narrow sector aperture and a wide linear scan pattern for relatively shallow imaging.

7. A method as defined in claim 1 wherein the step of transmitting ultrasound energy along sector lines includes transmitting along sector lines at both ends of the linear scan pattern to define sector scan patterns between a desired maximum angle α with respect a normal to the transducer array and the angle θ of the parallel lines, said composite scan pattern having a generally trapezoidal shape.

8. A method as defined in claim 7 wherein said parallel lines are equally spaced and said sector lines are equiangularly spaced.

9. A method as defined in claim 7 wherein at each end of the linear scan pattern, the center of the linear aperture coincides with the center of the sector aperture.

10. A method as defined in claim 1 wherein the step of transmitting ultrasound energy along sector lines includes transmitting ultrasound energy along sector lines with a full width sector aperture of said array for relatively deep imaging and transmitting ultrasound energy along sector lines with a reduced width sector aperture of said array that is narrower than said full width sector aperture for relatively shallow imaging and wherein the step of transmitting ultrasound energy along parallel lines includes increasing the number of parallel lines in the linear scan pattern when said sector lines are being transmitted through said reduced width sector aperture.

11. A method as defined in claim 10 wherein the step of transmitting ultrasound energy along parallel lines further includes the step of reducing the linear aperture of said array through which said parallel lines are transmitted near the ends of said linear scan pattern when said sector lines are being transmitted through said reduced width sector aperture.

12. An ultrasound imaging scanner comprising:
   an array of equally-spaced and equally-dimensioned ultrasound transducer
   a transmitter for transmitting ultrasound energy with said array (a) along parallel lines originating at different points on said array and oriented at a nonzero angle θ with respect to a normal to the array; and (b) along sector lines originating from an apex, said parallel lines defining a linear scan pattern and said sector lines defining a sector scan pattern, said transmitter including means for transmitting each of the sector lines of said sector scan pattern through a sector aperture of said array and means for transmitting each of the parallel lines of said linear scan pattern through a linear aperture of said array, wherein, at an end of the linear scan pattern, the sector aperture overlaps the linear aperture such that said sector scan pattern and said linear scan pattern abut to form a composite scan pattern in which said sector scan pattern and said linear scan pattern are nonoverlapping; and
   a receiver for receiving ultrasound echoes with said array along said parallel lines and said sector lines and for providing signals representative of an image along said parallel lines and said sector lines.

13. An ultrasound imaging scanner as defined in claim 12 wherein said transmitter includes means for transmitting along sector lines to form sector scan patterns at both ends of the linear scan pattern so that said composite scan pattern has a generally trapezoidal shape.

14. An ultrasound imaging scanner as defined in claim 12 wherein said transmitter includes means for transmitting ultrasound energy along sector lines with a full width sector aperture of said array for relatively deep imaging and means for transmitting ultrasound energy along sector lines with a reduced width sector aperture of said array that is narrower than said full width sector aperture for relatively shallow imaging, said transmitter further including means for increasing the number of parallel lines in the linear scan pattern when said sector lines are being transmitted through said reduced width sector aperture.

15. An ultrasound imaging scanner as defined in claim 14 wherein said transmitter further includes means for reducing the linear aperture of said array through which said parallel lines are transmitted near the ends of said linear scan pattern when said sector lines are being transmitted through said reduced width sector aperture.

16. A method for ultrasound imaging in a system including an array of ultrasound transducer elements, comprising the steps of:

transmitting ultrasound energy with said array along parallel lines originating at different points on said array, said parallel lines defining a linear scan pattern;

transmitting ultrasound energy with said array along sector lines originating from an apex, said sector lines defining a sector scan pattern, wherein each of the sector lines of said sector scan pattern is transmitted through a sector aperture of said array, wherein each of the parallel lines of said linear scan pattern is transmitted through a linear aperture of said array and wherein, at an end of the linear scan pattern, the sector aperture overlaps the linear aperture such that said sector scan pattern and said linear scan pattern abut to form a composite scan pattern in which said sector scan pattern and said linear scan pattern are nonoverlapping;

receiving ultrasound echoes with said array along said parallel lines and said sector lines and providing signals representative of an image along said parallel lines and said sector lines; and varying the width of said sector aperture and the width of said linear scan pattern, depending on the depth of a region of interest.

17. A method as defined in claim 16 wherein the step of varying the width of said sector aperture and the width of said linear scan pattern includes reducing the linear aperture of said array through which said parallel lines are transmitted near the ends of said linear scan pattern when said sector lines are being transmitted through a reduced width sector aperture.

18. An ultrasound imaging scanner comprising:

an array of ultrasound transducer elements;

first means for transmitting ultrasound energy with said array along parallel lines originating at different points on said array, said parallel lines defining a linear scan pattern, said first means including means for transmitting each of the parallel lines of said linear scan pattern though a linear aperture of said array;

second means for transmitting ultrasound energy with said array along sector lines originating from an apex, said sector lines defining a sector scan pattern, said second means including means for transmitting each of the sector lines of said sector scan pattern through a sector aperture of said array, wherein, at an end of the linear scan pattern, the sector aperture overlaps the linear aperture such that said sector scan pattern and said linear scan pattern abut to form a composite scan pattern in which said sector scan pattern and said linear scan pattern are nonoverlapping;

means for receiving ultrasound echoes with said array along said parallel lines and said sector lines and for providing signals representative of an image along said parallel lines and said sector lines; and means for varying the width of said sector aperture and the width of said linear scan pattern, depending on the depth of a region of interest.

19. A method for ultrasound imaging, comprising the step of:

transmitting ultrasound energy with an array of equally-spaced and equally-dimensioned ultrasound transducer elements along stepped scan lines originating at different points on said array, said stepped scan lines defining a stepped scan pattern;

transmitting ultrasound energy with said array along sector scan lines originating from an apex of a sector scan pattern, said sector scan lines defining said sector scan pattern, wherein each of the sector scan lines of said sector scan pattern is transmitted through a sector aperture of said array, wherein each of the stepped scan lines of said stepped scan pattern is transmitted through a stepped aperture of said array and wherein, at an end of the stepped scan pattern, the sector aperture overlaps the stepped aperture such that said sector scan pattern and said stepped scan pattern abut to form a composite scan pattern in which said sector scan pattern and said stepped scan pattern are nonoverlapping; and receiving ultrasound echoes with said array along said stepped scan lines and said sector scan lines and providing signals representative of an image along said stepped scan lines and said sector scan lines.

20. A method as defined in claim 19 wherein said array comprises a linear array, said stepped scan lines comprise parallel scan lines and said stepped scan pattern comprises a linear scan pattern.

21. A method as defined in claim 19 wherein said array comprises a curved linear array, said stepped scan lines comprise curved linear scan lines and said stepped scan pattern comprises a curved linear scan pattern.

22. A method as defined in claim 19 wherein each of said stepped scan lines is oriented at a nonzero angle with respect to a normal to the array.

23. A method as defined in claim 19 wherein the apex of said sector scan pattern is located on said array and coincides with the end of the stepped scan pattern.

24. A method as defined in claim 19 further including the step of varying the width of said sector aperture and the width of said stepped scan pattern, depending on the depth of a region of interest.

25. A method as defined in claim 19 wherein the step of transmitting ultrasound energy along sector scan lines includes transmitting along sector lines to form sector scan patterns at both ends of the stepped scan pattern.

26. An ultrasound imaging scanner comprising:

an array of equally-spaced and equally-dimensioned ultrasound transducer elements;

a transmitter for transmitting ultrasound energy with said array along stepped scan lines originating at different points on said array, and along sector scan lines originating from an apex of a sector scan pattern, said stepped scan lines defining a stepped scan pattern and said sector scan lines defining said sector scan pattern, said transmitter including means for transmitting each of the sector scan lines of said sector scan pattern through a sector aperture of said array and means for transmitting each of the stepped scan lines of said stepped scan pattern through a stepped aperture of said array, wherein, at an end of the stepped scan pattern, the sector aperture overlaps the stepped aperture such that said sector scan pattern and said stepped scan pattern abut to form a composite scan pattern in which said sector scan pattern and said stepped scan pattern are nonoverlapping; and a receiver for receiving ultrasound echoes with said array along said stepped scan lines and said sector scan lines and for providing signals representative of an image along said stepped scan lines and said sector scan lines.

27. An ultrasound imaging scanner as defined in claim 26 wherein said array comprises a linear array and wherein said transmitter for transmitting ultrasound energy along stepped scan lines includes means for transmitting ultrasound energy along parallel scan lines of a linear scan pattern.

28. An ultrasound imaging scanner as defined in claim 26 wherein said array comprises a curved linear array and wherein said transmitter for transmitting ultrasound energy along stepped scan lines includes means for transmitting ultrasound energy along curved linear scan lines of a curved linear scan pattern.

29. An ultrasound imaging scanner as defined in claim 26 wherein said stepped scan lines are oriented at a nonzero angle with respect to a normal to the array.

30. An ultrasound imaging scanner as defined in claim 26 wherein said transmitter includes means for transmitting ultrasound energy along sector scan lines with a full width sector aperture of said array for relatively deep imaging and means for transmitting ultrasound energy along sector scan lines with a reduced width sector aperture of said array that is narrower than full width sector aperture for relatively shallow imaging, said transmitter further including means for increasing the number of stepped scan lines in the stepped scan pattern when said sector scan lines are being transmitted through said reduced width sector aperture.

31. A method for ultrasound imaging, comprising the steps of:

transmitting ultrasound energy with a curved linear array of equally-spaced and equally-dimensioned ultrasound transducer elements along curved linear scan lines originating at different points on said array, said curved linear scan lines defining a curved linear scan pattern;

transmitting ultrasound energy with said array along sector scan lines originating from an apex of a sector scan pattern, said sector scan lines defining said sector scan pattern, wherein each of the sector scan lines of said sector scan pattern is transmitted through a sector aperture of said array, wherein each of the curved linear scan lines of said curved linear scan pattern is transmitted through a curved linear aperture of said array and wherein, at an end of the curved linear scan pattern, the sector aperture overlaps the curved linear aperture such that said sector scan pattern and said curved linear scan pattern abut to form a composite scan pattern in which said sector scan pattern and said curved linear scan pattern are nonoverlapping; and receiving ultrasound echoes with said array along said curved linear scan lines and said sector scan lines and providing signals representative of an image along said curved linear scan lines and said sector scan lines.

32. An ultrasound imaging scanner comprising:

a curved linear array of equally-spaced and equally-dimensioned ultrasound transducer elements;

a transmitter for transmitting ultrasound energy with said array along curved linear scan lines originating at different points on said array, and along sector lines originating from an apex of a sector scan pattern, said curved linear scan lines defining a curved linear scan pattern and said sector scan lines defining said sector scan pattern, said transmitter including means for transmitting each of the sector scan lines of said sector scan pattern through a sector aperture of said array and means for transmitting each of the curved linear scan lines of said curved linear scan pattern through a curved linear aperture of said array, wherein, at an end of the curved linear scan pattern, the sector aperture overlaps the curved linear aperture such that said sector scan pattern and said curved linear scan pattern abut to form a composite scan pattern in which said sector scan pattern and said curved linear scan pattern are nonoverlapping; and a receiver for receiving ultrasound echoes with said array along said curved linear scan lines and said sector scan lines and for providing signals representative of an image along said curved linear scan lines and said sector scan lines.

* * * * *